United States Patent
Gueary

(10) Patent No.: US 10,786,632 B2
(45) Date of Patent: Sep. 29, 2020

(54) VEIN STABILIZING DEVICE

(71) Applicant: Sherry V. Gueary, Laplace, LA (US)

(72) Inventor: Sherry V. Gueary, Laplace, LA (US)

( * ) Notice: Subject to any disclaimer, the term of this patent is extended or adjusted under 35 U.S.C. 154(b) by 185 days.

(21) Appl. No.: 16/050,041

(22) Filed: Jul. 31, 2018

(65) Prior Publication Data
US 2020/0038599 A1  Feb. 6, 2020

(51) Int. Cl.
*A61M 31/00* (2006.01)
*A61M 5/42* (2006.01)
*A61M 5/158* (2006.01)

(52) U.S. Cl.
CPC .......... *A61M 5/425* (2013.01); *A61M 5/158* (2013.01); *A61M 2205/584* (2013.01)

(58) Field of Classification Search
CPC .......... A61M 2205/584; A61M 5/158; A61M 5/425; A61M 5/3287; A61M 5/427; A61M 2005/1586
See application file for complete search history.

(56) References Cited

U.S. PATENT DOCUMENTS

| | | | | |
|---|---|---|---|---|
| 2,047,010 | A * | 7/1936 | Dickinson | A61M 5/3287 604/157 |
| 3,324,854 | A * | 6/1967 | Weese | A61M 5/425 604/115 |
| 4,403,987 | A * | 9/1983 | Gottinger | A61M 5/3287 604/115 |
| 2008/0269677 | A1* | 10/2008 | Cull | A61M 1/3653 604/116 |
| 2008/0300541 | A1* | 12/2008 | Rutkowski | A61M 5/425 604/116 |
| 2019/0160231 | A1* | 5/2019 | Dobie | A61M 5/42 |

* cited by examiner

*Primary Examiner* — Rebecca E Eisenberg
(74) *Attorney, Agent, or Firm* — Dunlap Bennett & Ludwig, PLLC

(57) ABSTRACT

A vein stabilizing device including a wire having a U-shaped bend forming a hook. An indicator disposed on the wire at a central portion of the U-shaped bend. The vein stabilizing device is used to quickly stabilized veins, eliminating the need for a tourniquet, decreasing the possibility of a blown vein and tissue death, and reducing the time required to start intravenous infusion.

5 Claims, 2 Drawing Sheets

VEIN STABILIZING DEVICE

BACKGROUND OF THE INVENTION

The present invention relates to inserting intravenous lines and, more particularly, to a device that aids in preparing intravenous lines.

In emergency situations hospitals, clinics and emergency rooms, medical professionals are called upon to quickly insert intravenous lines, or Ws, into a patient's vein to direct fluids and medications quickly into the bloodstream. Intravenous therapy is used to treat a variety of health conditions and to stabilize vital signs. Intravenous therapy works by delivering liquid medication through a catheter inserted into an open vein.

Most Ws are placed in a vein in the forearm or hand. A strong rubber tube, called a tourniquet, is wrapped around the upper arm to enlarge the veins in the lower arm by restricting blood flow through veins. A catheter is inserted into the skin through a needle. The needle is removed, leaving only the plastic catheter in the vein. Traditional methods of accessing the vein in many cases requires more time in locating, stabilizing and accessing the vein.

As can be seen, there is a need for a device that aids in preparing intravenous lines.

SUMMARY OF THE INVENTION

In one aspect of the present invention, a vein stabilizing device comprises: a wire comprising a U-shaped bend forming a hook; and an indicator disposed on the wire at a central portion of the U-shaped bend.

In another aspect of the present invention, a method of preparing an intravenous line comprises the steps of: providing a vein stabilizing device comprising: a wire comprising a U-shaped bend forming a hook; and an indicator disposed on the wire at a central portion of the U-shaped bend; locating a vein of a patient and cleaning skin over the vein; placing the hook directly over the vein to stabilize the vein such that the indicator is aligned with the vein; and puncture the vein just below the indicator with a needle.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention is a device that is used to help locate a vein, stabilize it, and allow the professional to keep track of the location site for puncture and intravenous access. The present invention may include a smooth hook with a handle (about 4 inches long and about 0.5 of inches wide). The hook of the present invention may be covered with a coated heat shrink-tubing for better gripping. The hook further includes a line located at the center of the hook. The present invention is used to quickly stabilized veins, eliminating the need for a tourniquet, decreasing the possibility of a blown vein and tissue death, and reducing the time required to start intravenous infusion.

Figure 1:
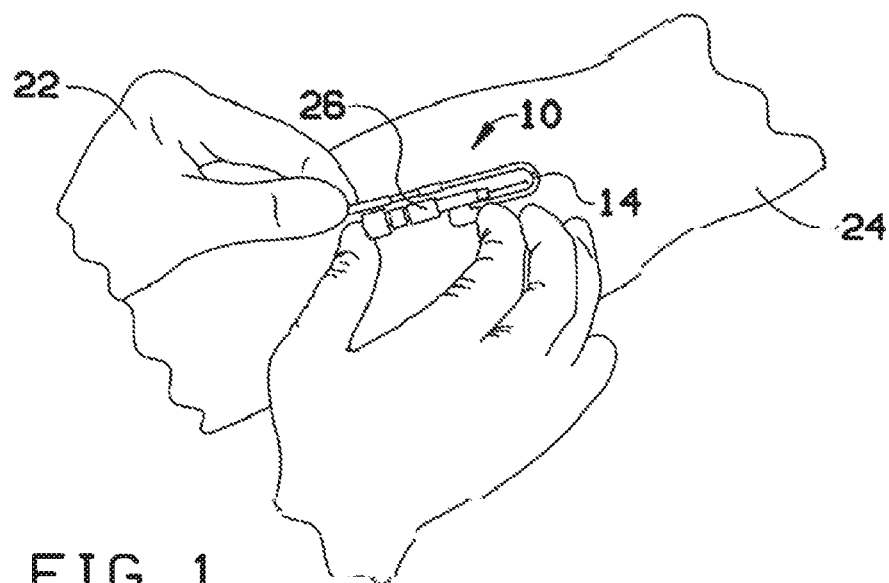
FIG. 1 is a perspective view of an embodiment of the present invention.
Figure 2:
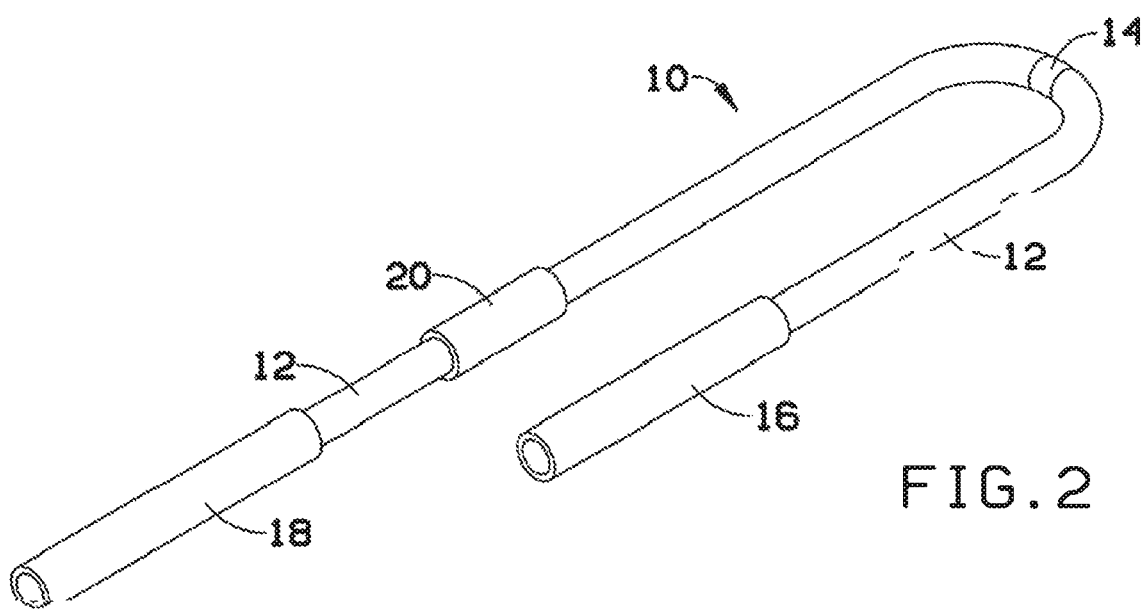
FIG. 2 is a perspective view of an embodiment of the present invention.
Figure 3:
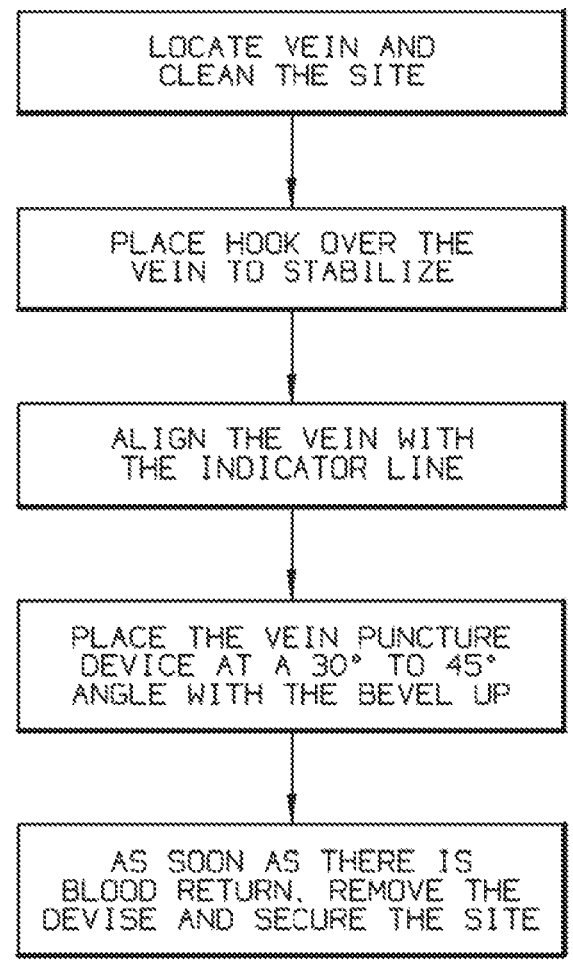
FIG. 3 is a flow chart of an embodiment of the present invention.

Referring to FIGS. 1 through 3, the present invention includes a vein stabilizing device 10. The vein stabilizing device 10 includes a wire 12 having a U-shaped bend forming a hook. The present invention further includes an indicator 14 disposed on the wire 12 at a central portion of the U-shaped bend.

The indicator 14 includes a marker which may be printed on an outer surface of the wire 12 or may be a ring coupled to the wire 12. The indicator 14 may be black, red or any color to provide a clear visual indicator 14 for the user. The indicator 14 is pressed against the vein to stabilize the vein and the user punctures the vein with a needle 26 just below the indicator 14.

The hook of the present invention includes a handle side and a stabilizing side with the U-shaped bend therebetween. The handle side and the stabilizing side are parallel relative to one another. In certain embodiments, the handle side is longer than the stabilizing side allowing the user 22 to easily grip the vein stabilizing device 10.

In certain embodiments, the present invention includes a first grip 18 coupled to the handle side. A second grip 20 is coupled to the handle side and is spaced apart from the first grip 18. A third grip 16 is coupled to the stabilizing side. The first grip 18 and second grip 20 are used by the user 22 to firmly grip the handle side of the vein stabilizing device 10. The third grip 16 is used to provide gripping on the patient's skin 24, preventing the vein stabilizing device 10 from sliding. The first grip 18, the second grip 20, and the third grip 16 may each be formed by a heat shrink tubing. Alternatively, the grips 18, 20, 16 may be made of a rubberized material, such as silicone and the like.

A method of using the present invention may include the following. Once the vein has been located, clean the site following standard venipuncture procedure for obtaining intravenous access. Then, place the hook portion of the present invention directly over the vein to stabilize it and then align the vein with the indicator line. The indicator line identifies the correct point of entry, which is directly in the center of the hook curve at the point indicated by the line. Next place the vein puncture device into the vein at about a 30 to 45 degree angle with the bevel up. As soon as there is a blood return (flashback) in the chamber, remove the present invention and secure the site.

A method of making the present invention may include the following. A piece of wire is cut to about 6 inches long. The wire is bent into the shape of a hook. In order to get the hook shape the wire may be bent at 4 inches and curve 180 degrees so that both sides of the hook are running parallel and are about 0.5 inches apart. The hook side of the device is about 1.5 inches long. Next, both the handle side and the hook side are both covered with heat shrink tubing for better gripping and patient comfortability.

It should be understood, of course, that the foregoing relates to exemplary embodiments of the invention and that modifications may be made without departing from the spirit and scope of the invention as set forth in the following claims.

What is claimed is:

1. A vein stabilizing device comprising:

a wire comprising a U-shaped bend forming a hook; and an indicator disposed on the wire at a central portion of the U-shaped bend, wherein the hook comprises a handle side and a stabilizing side with the U-shaped bend therebetween, wherein the handle side and the stabilizing side are parallel relative to one another, and wherein the handle side is longer than the stabilizing side.

2. The vein stabilizing device of claim 1, further comprising a first grip coupled to the handle side.

3. The vein stabilizing device of claim 2, further comprising a second grip coupled to the handle side spaced apart from the first grip, and a third grip coupled to the stabilizing side.

4. The vein stabilizing device of claim 3, wherein the first grip, the second grip, and the third grip are each formed by a heat shrink tubing.

5. A method of preparing an intravenous line comprising the steps of:

providing a vein stabilizing device comprising:
a wire comprising a U-shaped bend forming a hook; and
an indicator disposed on the wire at a central portion of the U-shaped bend;

locating a vein of a patient and cleaning skin over the vein;

placing the hook directly over the vein to stabilize the vein such that the indicator is aligned with the vein;

puncture the vein just below the indicator with a needle, wherein the hook comprises a handle side and a stabilizing side with the U-shaped bend therebetween, wherein the handle side and the stabilizing side are parallel relative to one another; and a first grip coupled to the handle side, a second grip coupled to the handle side spaced apart from the first grip, and a third grip coupled to the stabilizing side, wherein the first grip, the second grip, and the third grip are each formed by a heat shrink tubing.

* * * * *